United States Patent [19]
Deruyter et al.

[11] Patent Number: 5,637,796
[45] Date of Patent: Jun. 10, 1997

[54] MODULAR DEVICE FOR TESTING POROUS MATERIAL SAMPLES IN THE PRESENCE OF MULTIPHASE FLUIDS

[75] Inventors: Christian Deruyter, Rueil-Malmaison; Sylvain Prevot, Antony; François Kalaydjian, Rueil-Malmaison, all of France

[73] Assignee: Institut Francais du Petrole, Rueil Malmaison, France

[21] Appl. No.: 576,762

[22] Filed: Dec. 21, 1995

[30] Foreign Application Priority Data

Dec. 21, 1994 [FR] France ................................ 94 15546

[51] Int. Cl.$^6$ .................................................. E21B 49/02
[52] U.S. Cl. .................................. 73/152.09; 73/38
[58] Field of Search ..................... 73/38, 153, 152.07, 73/152.09, 152.11

[56] References Cited

U.S. PATENT DOCUMENTS

| | | | |
|---|---|---|---|
| 2,345,935 | 4/1944 | Hassler | 73/38 |
| 2,437,935 | 5/1948 | Brunner et al. | 73/38 |
| 2,705,418 | 4/1955 | Reichertz et al. | 73/38 |
| 2,821,680 | 1/1958 | Slusser et al. | 73/38 |
| 4,537,063 | 8/1985 | Barnaby | 73/38 |
| 4,562,726 | 1/1986 | Barnaby | 73/38 |
| 4,599,891 | 7/1986 | Brauer et al. | |
| 4,734,649 | 3/1988 | Barnaby | |
| 4,848,145 | 7/1989 | Blaschke et al. | 73/153 |
| 4,950,844 | 8/1990 | Hallmark et al. | 175/59 |
| 4,996,872 | 3/1991 | Mueller et al. | |
| 5,263,360 | 11/1993 | Blauch et al. | 73/38 |
| 5,325,723 | 7/1994 | Meadows et al. | |
| 5,493,226 | 2/1996 | Honarpour et al. | 73/153 |

FOREIGN PATENT DOCUMENTS 9200836  1/1992  France ........................ G01N 15/08

*Primary Examiner*—Hezron E. Williams
*Assistant Examiner*—Jay L. Politzer
*Attorney, Agent, or Firm*—Antonelli, Terry, Stout & Kraus, LLP

[57] ABSTRACT

The device is suited for taking measurements on more or less porous samples of geologic origin, for example physical parameters: wettability, capillary pressure, saturations, etc, in the presence of multiphase fluids that are displaced during drainage and imbibition operations. It comprises a modular cell whose length can be suited to that of a sample by adding tubular sections (24) of equal or different lengths that are interposed between two sleeves (1A, 1E). The containment cell is provided at its opposite ends with ends (13, 14) possibly fitted with semipermeable membranes, to which fluid lines (15, 16) are connected. Joining pieces (9) possibly provided with a control valve (10) can be fitted to all the sleeves (1A to 1E) for the connection of pressure detectors, gas injection means, etc. The device can be applied to optimization of hydrocarbon recovery in underground reservoirs.

15 Claims, 2 Drawing Sheets

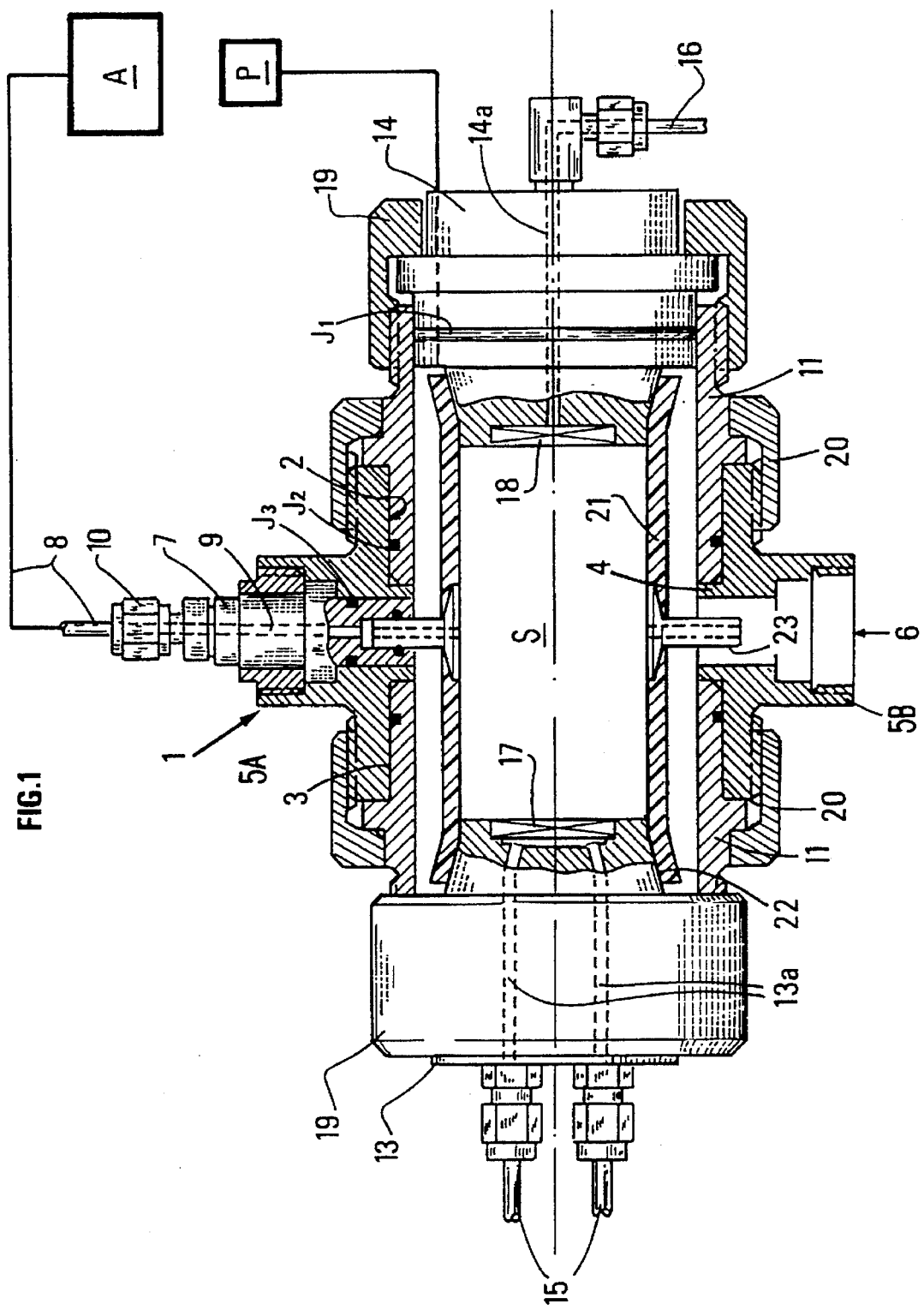

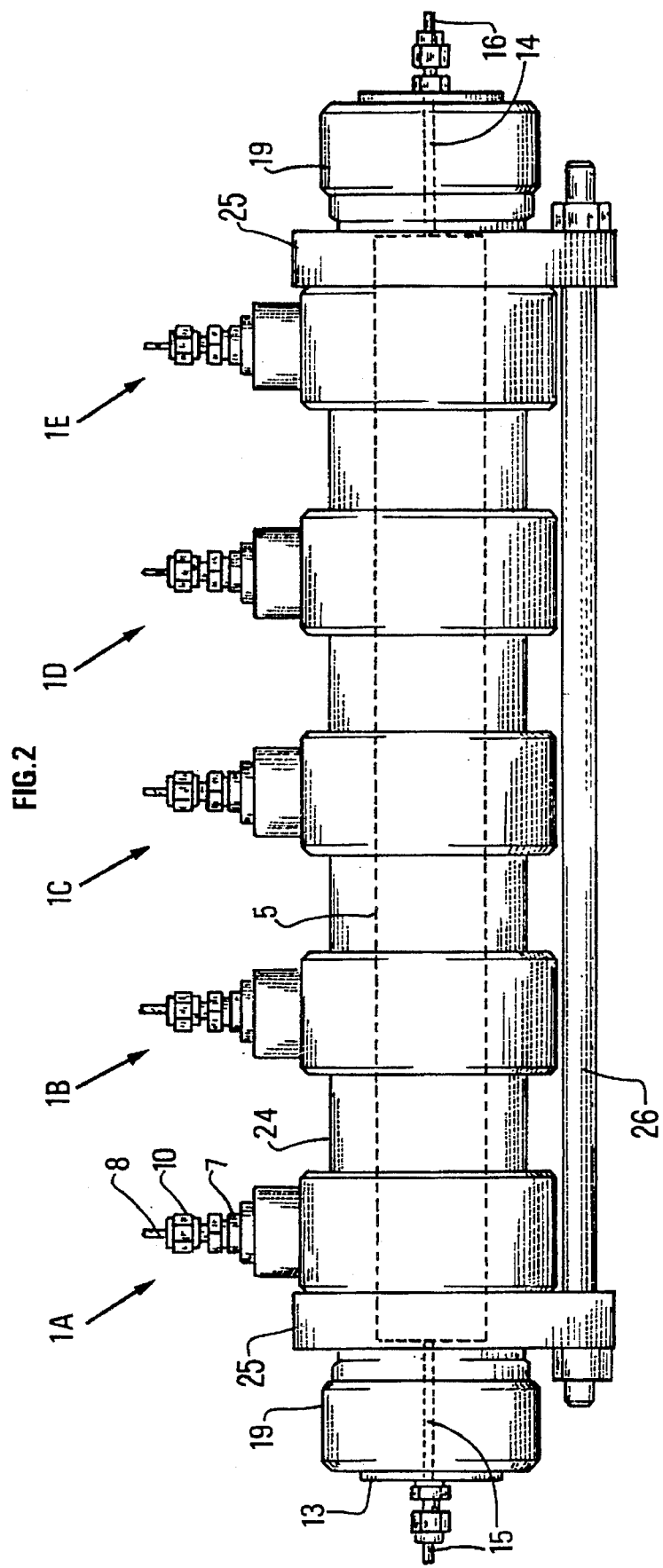

MODULAR DEVICE FOR TESTING POROUS MATERIAL SAMPLES IN THE PRESENCE OF MULTIPHASE FLUIDS

FIELD OF THE INVENTION

The object of the present invention is a modular cell for testing porous material samples in the presence of fluids.

The device according to the invention is suited for testing for example geologic samples and for determining various parameters such as the capillary pressure of rocks during drainage or imbibition phases, their wettability indices, their relative permeabilities, their resistivity indices, etc.

The device according to the invention notably applies to the petroleum sphere for determining the characteristics of rocks that have been taken in formations containing or likely to contain hydrocarbons.

The device also applies to civil engineering for example for the hydrology of grounds in order to appraise their degree of pollution for example, or to the building industry for testing building materials in order notably to decide on waterproofing treatments for example.

BACKGROUND OF THE INVENTION

The saturation values that depend on parameters such as the wettability and the interfacial tension must be known at any point in order to determine the distribution of the oil and gas volumes in a reservoir or an aquifer. To that effect, the wettability of rocks with respect to the water and the oil that can be contained therein is determined. To that effect, rock drainage operations have to be carried out, i.e. a displacement of the fluids intended to decrease the water saturation, followed by imbibition operations, this term referring to a displacement of the fluids allowing the water saturation (Sw) of the rock to be increased. The capillary pressure at a point of a porous material containing two fluids such as water and oil in the continuous phase is defined, as it is well-known, as the difference Pc at equilibrium between the pressure P(oil) of the oil and the pressure P(water) of the water.

The knowledge of various parameters and notably of the wettability of rocks is useful notably when enhanced recovery operations are to be carried out in a formation by draining the effluents it contains by injection of a pressurized fluid, and when preliminary tests have to be carried out to select the most appropriate fluid (water or gas) for displacing the effluents.

Different types of devices are used to carry out laboratory drainage and imbibition operations. Sample bars are generally placed in a cell. At its opposite ends, the cell comprises two ends communicating with means for displacing pressurized fluids through the sample tested. Measuring means are placed at different points along the bar in order to measure different parameters: pressures, saturations, electric resistivity, etc. The sample bar can be placed in an elastomer containment sheath compressed by injection of a pressurized fluid.

Different devices for measuring the physical parameters of porous solid samples are described for example in patent applications FR-2,603,040, EN. 93/09,481 or EN-94/10,783 filed by the claimant or in patents U.S. Pat. Nos. 4,868,751; 5,506,542 or 5,069,065.

SUMMARY OF THE INVENTION

The device according to the invention allows fluids to be displaced through a more or less porous solid sample in order to measure some of its physical parameters. It comprises a sample containment cell consisting of a tubular cell body provided with a cell end at both ends, and means for obtaining a displacement of pressurized fluids through the sample.

It comprises at least one connecting sleeve provided with opposite cavities and two end stop rings associated respectively with the two ends by first fastening means, provided each with a tubular extension whose section is suited to that of the cavities of each connecting sleeve, second fastening means for pressing each end stop ring against a connecting sleeve, and seal means for insulating the containment cell from the outside.

According to a first embodiment, each end stop ring comprises means for fastening it onto a connecting sleeve.

According to another embodiment, the device comprises at least one tie rod for connecting end stop rings to each other.

The device comprises for example at least two connecting sleeves and at least one tubular section of determined length interposed between two connecting sleeves, the diameter of the end parts of this tubular section being suited to that of the cavities of each connecting sleeve.

The device can thus comprise several tubular sections interposed between several connecting sleeves, possibly of different lengths, selected from a set of available sections, so as to obtain a cell whose length is suited to that of the porous sample bar to be tested.

The device can also comprise an elastic sheath delimiting a containment cell with the ends, and pressure means for pressing the sheath against the porous sample.

According to an embodiment, the device can comprise one or several semipermeable membranes placed in the neighbourhood of the cell ends.

According to an advantageous embodiment, each connecting sleeve comprises at least one radial lengthening piece, a radial bore and means for establishing a connection, through this lengthening piece, between the inside of the cell and an outer apparatus that can be for example a measuring instrument such as a pressure detector or a gas injection means. These connection means can be for example a tube provided with a connecting piece that can be screwed into a bore provided through each radial lengthening piece and possibly fitted with a needle valve and/or semipermeable membranes, this tube communicating with a gas source or a pressure detector inlet.

In the case where the sample is contained in an elastic sheath, each connecting sleeve comprises a housing for a rigid eyelet crossing the sheath and allowing the radial channel of each sleeve to communicate with the sample.

On account of its modular design, the device according to the invention can be arranged to receive a more or less long sample. The connecting sleeves that can be interposed over the length of the sample allow very diverse injection and/or measuring means to be adapted in order to meet imposed test conditions.

BRIEF DESCRIPTION OF THE DRAWINGS

Other features and advantages of the device according to the invention will be clear from reading the description hereafter of embodiments given by way of non limitative example, with reference to the accompanying drawings in which:

FIG. 1 shows a first embodiment of the device, and

FIG. 2 shows a second embodiment consisting of the assemblage of several tubular sections and several connecting sleeves interposed so as to lengthen a containment cell.

DESCRIPTION OF THE PREFERRED EMBODIMENTS

According to the embodiment of FIG. 1, the device comprises a tubular connecting sleeve 1 provided with two cylindrical cavities 2, 3 on either side of a central shoulder 4. The sleeve comprises for example two radial lengthening pieces 5a and 5b, the second forming the continuation of the first one, provided each with a central bore 6 in which the joining piece 7 of a tube 8 can be screwed. This radial joining piece 7 comprises for example a needle valve 9. It can be actuated by the rotation of a ring 10 and communication with tube 8 can be controlled thereby.

The device also comprises two end stop rings 11 provided each with a tubular extension 12 suited for fitting into the cavities 2, 3 of each connecting sleeve 1. At each end, the device comprises an end 13, 14 crossed right through by one or several channels 13A, 14A to which lines 15, 16 linked with fluid pumping circuits (not shown) can be connected.

Semipermeable membranes 17, 18 of variable thickness can be possibly interposed between the sample S to be tested and the two ends 13, 14. They are selected as a function of the fluids to be displaced in the sample.

A threaded ring 19 suited for being screwed onto an end stop ring 11 in order to cause each of the cell ends 13, 14 to rest against an end face of the sample S is fastened to each end. Another threaded ring 20 immovably fastened in translation to each stop ring allows the tubular extensions 12 of the stop rings 11 to fit into the bottom of the cavities of sleeve 1.

For some applications where a radial pressure is to be exerted on sample S, the latter is placed in an elastic sheath 21. Each of the cell ends 13, 14 comprises a truncated end part suited for fitting under the sheath at each of its ends so as to delimit therewith a containment cell. The annular space around sheath 21 communicates with means P delivering a pressurized fluid by means of a port (not shown). The joining piece 7 fastened to each radial lengthening piece 5a, 5b along the axis thereof comprises a housing for a rigid eyelet 23 crimped through sheath 21 so as to communicate the sample S contained therein with line 8.

Seals J1, J2, J3, J4 are interposed between ends 13, 14, stop rings 11, sleeves 1 and around each radial joining piece 7 so as to insulate the containment cell from the outside medium.

According to the embodiment of FIG. 2, the sample containment cell can be lengthened at will by interposing one or several tubular sections 24 whose outside diameter is substantially identical to that of the previous tubular extensions 12, so as to fit into the symmetrical cavities of each connecting sleeve 1. The different parts making up the device can be immovably fastened to each other as previously by screwing rings 20 (FIG. 1) to the end sleeves 1A, 1E. Another way to fasten them immovably to each other consists, as in this case, in joining the end stop rings 11 by means of one or several tie rods 25.

With four short tubular sections interposed between five connecting sleeves 1, as shown in FIG. 2 by way of example, a measuring cell can be built up for a sample of great length with five radial access points distributed over its length, in controlled communication with as many lines 8. The configuration can be changed for a given sample length by decreasing the number of interposed sleeves 1 and by lengthening the interposed tubular sections.

Lines 8 are used for connecting the inside of the cell, at the level of each lengthening piece 5a, 5b to a apparatus A. It can be for example a pressure detector in order to measure the pressure of the fluids in the sample at differents drainage or imbibition operation stages.

As described in the claimant's patent application EN-94/. . .., these pressure tappings can be made selective by interposing one or several membranes in the channel 9 of each joining piece 7 (FIG. 1).

The apparatus A connected by lines 8 can also be a pressurized gas source within the scope of operations of physical parameter measurements of a sample where multiphase fluids are displaced.

We claim:

1. A device for achieving fluid displacements in a porous solid sample positioned in a one piece flexible sheath provided with opposite end parts in order to measure some physical parameters of the sample, said device comprising a sample containment cell including a connecting sleeve, two tubular end elements each having a tubular extension, the connecting sleeve being provided with a central projection and with two opposite cavities on either sides of the projection, said cavities each receiving a tubular extension, means for tightly securing the tubular end elements to the connecting sleeve whereby the tubular extensions are pressed in abutment against the central projection, two cell ends provided each with a frustro-conical head portion for closing opposite end parts of the sheath in which the porous solid sample is located, fastening means for tightly securing the cell ends, respectively, to the tubular end elements, first pressure means for effecting a pressurized fluid displacement through the sample, and second pressure means for pressing the sheath against the sample.

2. A device for achieving fluid displacements in a porous solid sample provided with opposite end parts in order to measure some physical parameters of the sample, said device comprising a sample containment cell including at least two connecting sleeves, at least two tubular end elements and at least one intermediate tubular part of determined length interposed between any two adjacent connecting sleeves, each connecting sleeve being provided with a central hollow projection, said cavities each being adapted to receive an end of said tubular end element and an intermediate tubular part, two cell ends provided each with a frustro-conical head for closing said opposite end parts of the sheath, securing means for tightly fitting the tubular end elements, the at least one intermediate tubular part and the cell ends together whereby the tubular end elements and the at least one intermediate tubular part are pressed in abutment against the central projection of each of the connecting sleeves, first pressure means for obtaining a pressurized fluid displacement through the sample, and second pressure means for pressing the sheath against the sample.

3. A device according to claim 2 wherein the securing means includes first fastening means for tightly securing said at least one intermediate tubular part and each tubular end element to the connecting sleeves and second fastening means for tightly securing the cell ends, respectively, to the tubular end elements.

4. A device according to claim 3, wherein the first fastening means includes flanges associated with at least one tie rod.

5. A device according to claim 2 comprising several intermediate tubular parts interposed between several connecting sleeves selected from a set of tubular sections of equal or of different lengths, so as to obtain a cell whose length is suited to that of a porous sample bar to be tested.

6. A device according to claim 1, comprising one or several semipermeable membranes placed close to at least one end of the cell.

7. A device according to claim 2, comprising one or several semipermeable membranes placed close to at least one end of the cell.

8. A device according to claim 1, further comprising a rigid eyelet crossing the sheath, each connecting sleeve comprising at least one radial insert, each provided with a radial bore, and connecting means for establishing a connection, through said radial insert and the eyelet, between the inside of the sheath and an outside detecting apparatus.

9. A device according to claim 2, further comprising a rigid eyelet crossing the sheath, each connecting sleeve comprising at least one radial insert, each provided with a radial bore, and connecting means for establishing a connection, through said radial insert and the eyelet, between the inside of the sheath and an outside detecting apparatus.

10. A device as claimed in claim 8, wherein said connecting means includes a tube including a valve means, said tube being provided with a connecting piece screwed into a bore provided through each radial insert, and communicating with said outside detecting apparatus.

11. A device as claimed in claim 9, wherein said connecting means includes a tube including a valve means, said tube being provided with a connecting piece screwed into a bore provided through each radial insert, and communicating with said outside detecting apparatus.

12. A device as claimed in claim 8, wherein said connecting means is fitted with at least one semipermeable membrane.

13. A device as claimed in claim 9, wherein said connecting means is fitted with at least one semipermeable membrane.

14. A device as claimed in claim 8, wherein the apparatus is a gas injection means.

15. A device according to claim 9, comprising one or several semipermeable membranes placed close to at least one end of the cell.

* * * * *